(12) United States Patent
Halsne

(10) Patent No.: US 11,207,535 B2
(45) Date of Patent: Dec. 28, 2021

(54) FAULT IDENTIFICATION LOGIC IN AN EXTERNAL READINESS MONITOR FOR AN AUTOMATED EXTERNAL DEFIBRILLATOR (AED)

(71) Applicant: KONINKLIJKE PHILIPS N.V., Eindhoven (NL)

(72) Inventor: Eric Grant Halsne, Kenmore, WA (US)

(73) Assignee: Koninklijke Philips N.V., Eindhoven (NL)

( * ) Notice: Subject to any disclaimer, the term of this patent is extended or adjusted under 35 U.S.C. 154(b) by 515 days.

(21) Appl. No.: 16/086,813

(22) PCT Filed: Mar. 21, 2017

(86) PCT No.: PCT/EP2017/056626
§ 371 (c)(1),
(2) Date: Sep. 20, 2018

(87) PCT Pub. No.: WO2017/162627
PCT Pub. Date: Sep. 28, 2017

(65) Prior Publication Data
US 2019/0060657 A1    Feb. 28, 2019

Related U.S. Application Data

(60) Provisional application No. 62/311,049, filed on Mar. 21, 2016.

(51) Int. Cl.
*A61N 1/39*   (2006.01)

(52) U.S. Cl.
CPC .......... *A61N 1/3931* (2013.01); *A61N 1/3904* (2017.08); *A61N 1/3937* (2013.01); *A61N 1/3968* (2013.01); *A61N 1/3993* (2013.01)

(58) Field of Classification Search
CPC ........................... A61N 1/3931; A61N 1/3904
USPC ............................................................ 607/5
See application file for complete search history.

(56) References Cited

U.S. PATENT DOCUMENTS

| | | | |
|---|---|---|---|
| 2004/0049233 A1* | 3/2004 | Edwards | A61N 1/3931 607/5 |
| 2006/0149323 A1 | 7/2006 | Merry et al. | |
| 2007/0078487 A1 | 4/2007 | Vaisnys et al. | |
| 2008/0300659 A1 | 12/2008 | Matos | |
| 2011/0060378 A1 | 3/2011 | Tuysserkani | |
| 2015/0321020 A1 | 11/2015 | Gumbrell | |

FOREIGN PATENT DOCUMENTS

| | | |
|---|---|---|
| FR | 2946539 | 12/2010 |
| JP | 2007058442 A | 3/2007 |
| JP | 2009225835 A | 10/2009 |
| JP | 3156737 U | 12/2009 |
| WO | 9844989 A1 | 10/1998 |
| WO | 2006102427 A2 | 9/2006 |

\* cited by examiner

*Primary Examiner* — Nadia A Mahmood

(57) ABSTRACT

A monitoring device for monitoring the readiness state of an automated external defibrillator (AED) and communicating the state to a remote receiver is described. The method uses a fault identification logic operable to detect an AED with a depleted battery. An associated method is described as well. The monitoring device captures both of a parameter related to the activation of the AED fault alert indicator and a second parameter that indicates a positive AED battery state.

13 Claims, 8 Drawing Sheets

AED AND COMMUNICATOR

AED MONITORING DEVICE SYSTEM

FAULT IDENTIFICATION LOGIC IN AN EXTERNAL READINESS MONITOR FOR AN AUTOMATED EXTERNAL DEFIBRILLATOR (AED)

CROSS-REFERENCE TO PRIOR APPLICATIONS

This application is the U.S. National Phase application under 35 U.S.C. § 371 of International Application No. PCT/EP2017/056626, filed on Mar. 21, 2017, which claims the benefit of U.S. Provisional Patent Application No. 62/331,049, filed on Mar. 21, 2016. These applications are hereby incorporated by reference herein.

BACKGROUND

The invention relates to an improved apparatus and method for maintaining an automated external defibrillator (AED). In particular, the invention pertains to a monitoring device which captures a state of readiness of a co-located AED, and subsequently communicates the state to a remote service provider location.

FIG. 1 illustrates a prior art AED 100 is shown in a top perspective view. The AED 100 is housed in a rugged polymeric case 102 which protects the electronic circuitry inside the case and also protects the layperson user from shocks. Such AEDs are generally mounted in distinctive locations such as on walls in high traffic areas and with signage to mark and indicate their locations, or the AED may be placed anywhere in the home. A home AED, like other AEDs, may go an extended period of time without use, and so it may be stored in a location lacking prominence such as in a closet or drawer.

Attached to the case 102 by electrical leads is a pair of electrode pads. In the embodiment of FIG. 1 the electrode pads are in a sealed airtight cartridge 104 located in a recess on the top side of the AED 100. The electrode pads are accessed for use by pulling up on a handle 108 which allows removal of a plastic cover over the electrode pads. A small ready light 106 informs the user of the readiness of the AED. In this embodiment the ready light blinks after the AED has been properly set up and is ready for use. The ready light 106 is on constantly when the AED is in use, and the ready light remains off when the AED needs attention.

Below the ready light is an on/off button 110. The on/off button is pressed to turn on the AED for use. To turn off the AED a user holds the on/off button down for one second or more. A caution light 114 flashes when information is available for the user. The user depresses the information button to access the available information. A caution light 114 blinks when the AED is acquiring heartbeat information from the patient and lights continuously when a shock is advised, alerting the rescuer and others that no one should be touching the patient during these times. Interaction with the patient while the heart signal is being acquired can introduce unwanted artifacts into the detected ECG signal. A shock button 116 is depressed to deliver a shock after the AED informs the rescuer that a shock is advised. An infrared port 118 on the side of the AED is used to transfer data between the AED and a computer. This data port find used after a patient has been rescued and a physician desires to have the AED event data downloaded to his or her computer for detailed analysis.

A speaker 120 provides voice instructions to a rescuer to guide the rescuer through the use of the AED to treat a patient. A beeper 122 is provided which "chirps" when the AED needs attention such as electrode pad replacement or a new battery. The annunciator includes a vibrating diaphragm to generate acoustic energy. An exemplary type of annunciator is a piezo-electric disk beeper such as the 5V audio transducer EMX-7T05SCL63, manufactured by the Myn Tahl Corporation of Fremont Calif. Of course, beeper 122 requires AED battery power to operate.

FIG. 2 illustrates a typical Beep Sequence 202 which issues from an AED beeper 122 as a result of an audible fault alert 200 that is discovered during a device self-test. After the fault is detected, AED 100 drives the beeper 122 to issue a series of beep 204 that are 125 mS long, separated by a beep interval 206 of about 875 mS. The beep frequency in this example is 2400 Hz. Beep Sequence 202 is three "chirps", which indicates a fault that renders the device "not ready for use." In the case of faults which require a user's attention but that are not serious enough to render the device inoperable, such as a mild low battery condition, the beep sequence may be just one "chirp." The beep sequence is repeated every 8 seconds until either the fault is corrected or until the battery dies.

Other AEDs may have different beep sequences, frequencies, and repetition intervals. In all cases, however, the particular sequence unambiguously indicates a self-test fault and is of a pre-determined and known acoustic signature.

One problem in the prior art is that the self-test fault alerting is local. If a user is not within visual or audible range of the AED when it begins to issue an alert, then corrective action is not possible. If the alert continues until the AED battery is depleted, then it is further possible that the device will not be ready to use when needed. If the AED battery is completely depleted, there may be no obvious external indication that the device is non-functional. The AED will not chirp in this condition. If the visual readiness indicator is not fail-safe, i.e. does not provide a positive indication that the AED is indeed dead even without any power, the user may assume that the device is ready for use. Thus, unnecessary delay to treatment of a cardiac arrest victim may ensue.

BRIEF SUMMARY

The inventor here describes an apparatus and method that overcome the problems with the prior art AEDs by describing a device, preferably located adjacent to an AED storage location, that monitors the status of the AED and communicates that status to a remote location. Several features of the invention ensure that conditions in which an AED that is completely depleted of battery power and/or an AED that has been removed from the location are affirmatively reported to the remote location.

In some embodiments, a method of sensing an operating status of a defibrillator having both of a fault indicator and a power supply indicator may include providing (702) a monitoring device disposed adjacent the defibrillator, sensing a lack of an activation of the fault indicator by the fault indicator sensor for a predetermined period of time, second sensing a lack of the power supply indicator by the power sensor for a second predetermined period of time, and generating a defibrillator failure operating status output signal responsive to both of the sensing and the second sensing steps.

In some embodiments, the monitoring device may include a fault indicator sensor disposed adjacent the defibrillator fault indicator and operable to detect an activation of the fault indicator, a power sensor disposed adjacent the defibrillator power supply indicator and operable to detect an activation of the power supply indicator, a hardware processor in electrical communication with both of the fault indicator sensor and the power sensor, and an output in communication with the hardware processor for providing a signal indicative of the defibrillator operating status.

In some embodiments, such a method and apparatus may further include providing a transmitter in communication with the monitoring device hardware processor and/or transmitting a defibrillator failure operating status message from the transmitter responsive to the generating step.

In other embodiments, the second predetermined period of time corresponds to a scheduled self-test activation time of the defibrillator. The second sensing step may recur on a daily basis.

In some embodiments, the power sensor is an optical sensor arranged to detect a lighted defibrillator power supply indicator. The optical sensor may be arranged to detect an infrared data communications signal stream, such as that corresponding to an Infrared Data Association (IrDA) signal, which the AED automatically transmits on a scheduled and recurring basis.

In some embodiments, the fault indicator sensor may include one selected from the group of a microphone and a sensor operable to detect a non-audible parameter related to a diaphragm motion of a fault indicator diaphragm.

In some embodiments, the fault indicator sensor consists of one selected from the group of an optical sensor arranged to detect an LCD icon, a photoelectric sensor arranged to detect a flashing indicator light, a camera arranged to detect a defibrillator display panel, and a magnetic sensor arranged to detect an electromechanical status indicator signal.

In some embodiments, such a method may further include sensing an activation of the fault indicator by the fault indicator sensor and/or generating a defibrillator failure operating status output signal responsive the sensing of the activation.

In other embodiments, a defibrillator status communicator system may include a defibrillator having a fault indicator output and a power supply indicator output, an electronic monitoring module disposed external to the defibrillator and adjacent to both of the fault indicator output and the power supply indicator output and/or a wireless transmitter in communication with the output, the transmitter operable to transmit a defibrillator status report based on a function of the signal.

In some embodiments, such a system may further include a remote service provider computer in wireless communication with the wireless transmitter and operable to receive the defibrillator status report. The remote service provider computer may automatically generate a service alert message responsive to the defibrillator status report.

As used herein for purposes of the present disclosure, the term "processor" is used generally to describe various apparatus relating to the operation of a ventilator apparatus, system, or method. A processor can be implemented in numerous ways (e.g., such as with dedicated hardware) to perform various functions discussed herein. A processor is also one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more computer storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In various implementations, the terms "low-power standby circuit", "clock", "state change monitor", "comparator" apply to components that are generally known in the art, and may be embodied in conventional microprocessors, application specific integrated circuits (ASICs), and field-programmable gate arrays (FPGAs), or may be integrated into the above described processor or controller. "Outputs" and "signals" may be understood to be electrical or optical energy impulses which represent a particular detection or processing result.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
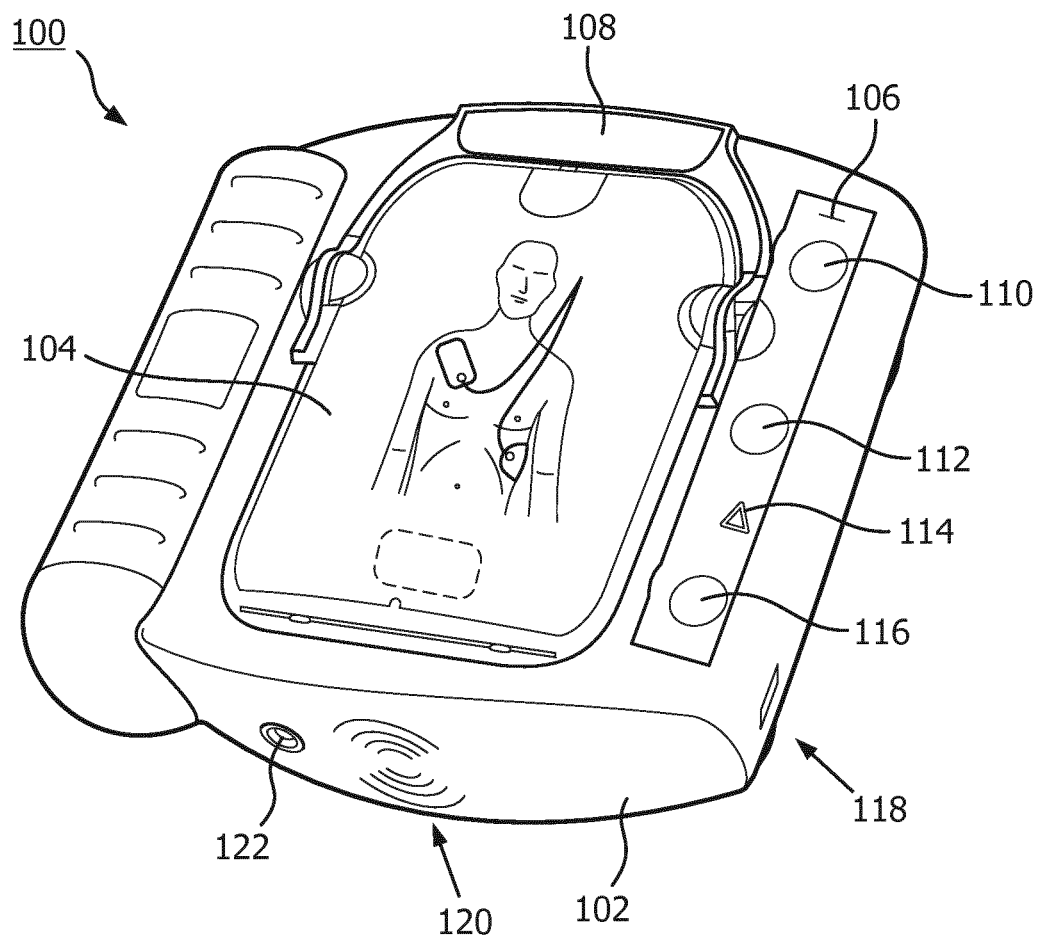
FIG. 1 illustrates a prior art AED shown in a top perspective view.
Figure 2:
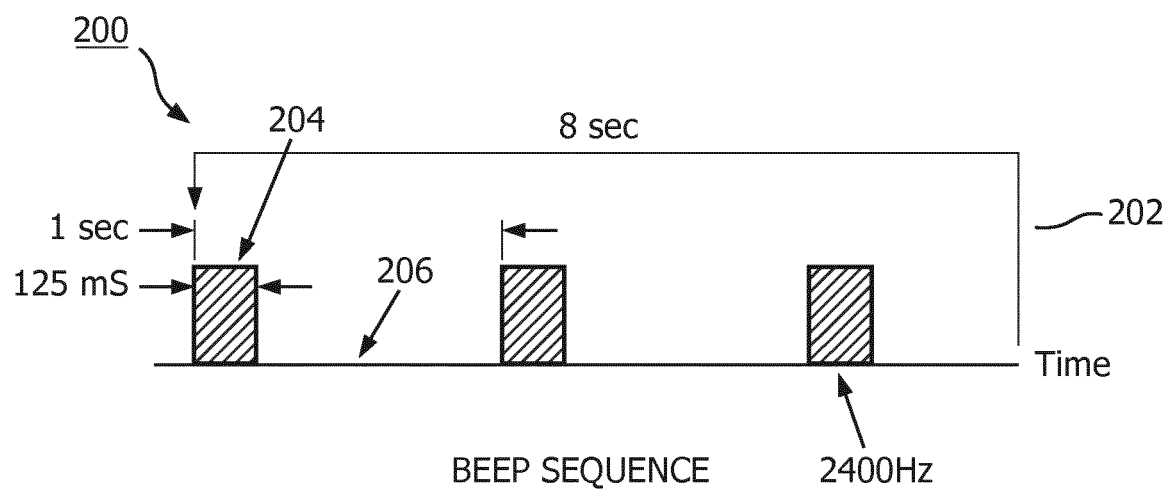
FIG. 2 illustrates an exemplary audible alert sequence from a prior art AED.

The phrases "in one embodiment", "in various embodiments", "in some embodiments", and the like are used repeatedly. Such phrases do not necessarily refer to the same embodiment. The terms "comprising", "having", and "including" are synonymous, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to or combined, without limiting the scope to the embodiments disclosed herein.

Figure 3:
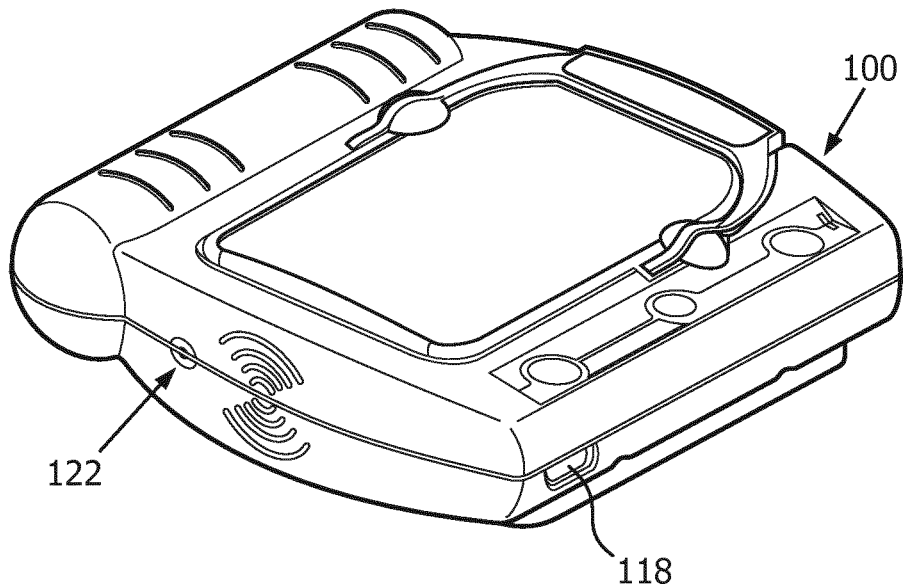
FIG. 3 illustrates an exemplary monitoring device 300 in accordance with one embodiment of the invention.
Figure 3:
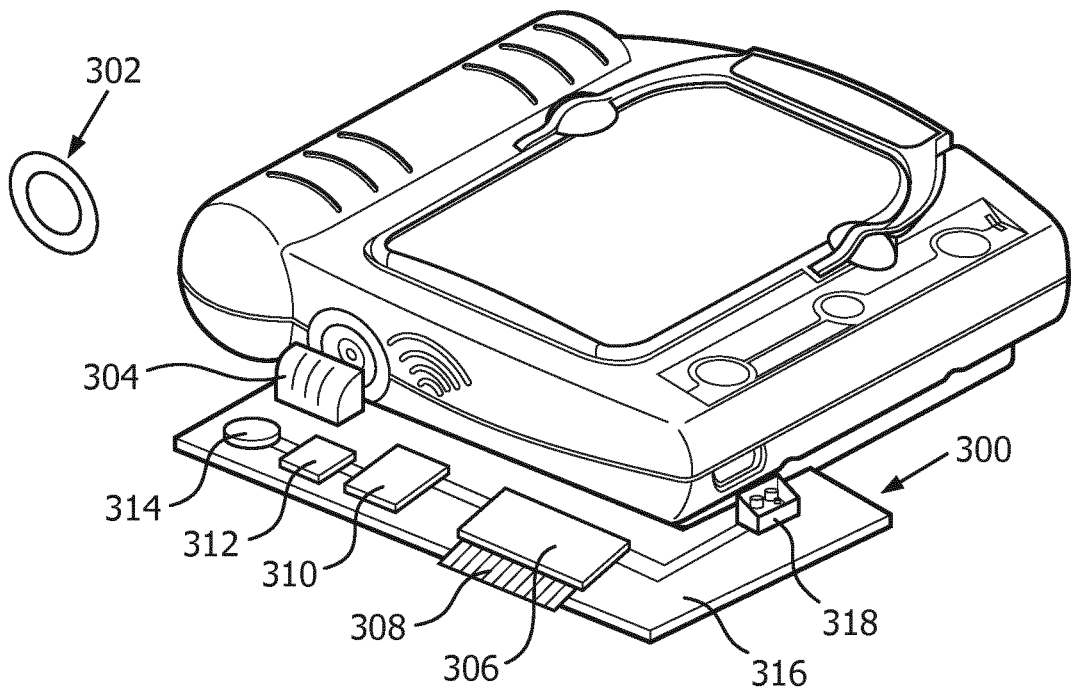

FIG. 3 illustrates an exemplary monitoring device 300 for sensing the operating status of a defibrillator or AED 100, in accordance with one embodiment. As previously described, AED 100 includes an audible annunciator 122 with a vibrating diaphragm. AED 100 may also include infrared port 118.

Monitoring device 300 for sensing an operating status of AED 100 is shown in a preferred position disposed adjacent the defibrillator. The disposition is such that a sensor 304 is disposed adjacent the annunciator. Sensor 304 in particular is of a type that is operable to detect a non-audible parameter that is related to the motion of the vibrating diaphragm in the annunciator. Monitoring device 300 includes a hardware processor 306 that is disposed in communication with sensor 304. When sensor 304 provides an input to the hardware processor 306 relating to an actuation of the annunciator, processor 306 issues a signal at output 308 that corresponds to the detection. As will be described, output 308 is preferably provided to a wireless transmitter that is operable to transmit a corresponding defibrillator status report to a remote receiver.

Also shown on monitoring device 300 is a low-power standby circuit 310, clock 312 and power supply 314 in communication with the hardware processor 306. These components enable to monitoring device 300 to operate for extended periods, e.g. months, without an external power source, by placing the monitoring device 300 in a low-power standby mode for most of the time. The clock 312 drives the standby circuit 310 to activate hardware processor 306 on a predetermined periodicity, and for a brief predetermined time. The activation interval is selected such that the interval that will capture any annunciator-induced vibration if there is one.

Components for the monitoring device 300 are disposed on one or more substrate 316, such as a printed circuit board.

Also shown is an optional decal 302 that is arranged to be applied to the AED 100 around or next to the annunciator. The decal is selected to be used to increase the sensitivity of sensor 304 to annunciator-induced vibration. Hence, the decal 302 may be electrically conductive if the sensor 304 is sensitive to electrical changes induced by the diaphragm motion, or may be optically reflective if the sensor 304 is sensitive to vibrational, reflective, or positional changes induced by the diaphragm motion. Decal 302 preferably is adhesively applied to the AED 100.

Not shown in FIG. 3 for ease of viewing the components is an enclosure for monitoring device 300 that surrounds at least one side of AED 100. The enclosure is preferably integrated with the AED 100 carrying case or the wall mount.

Figure 4:
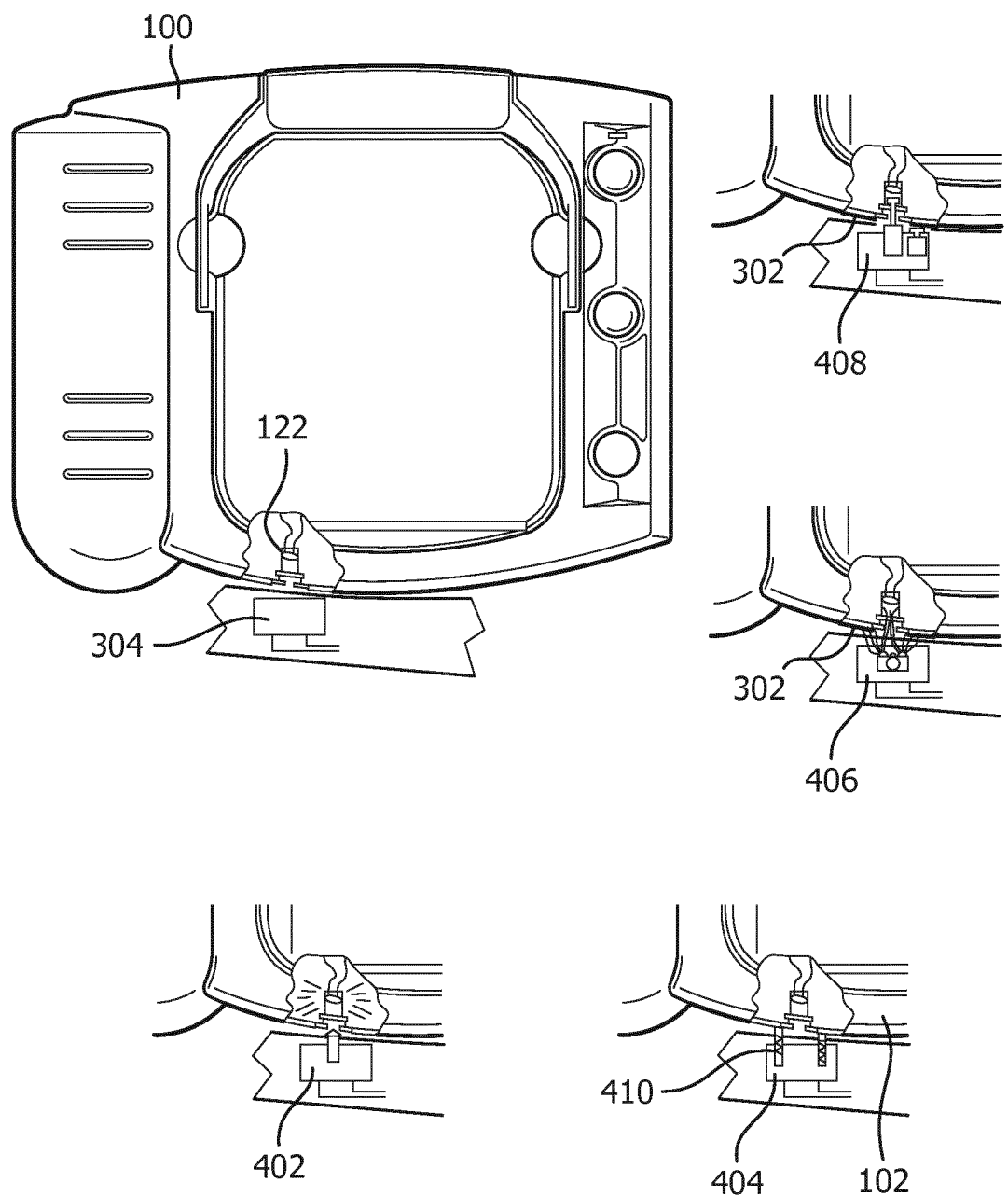
FIG. 4 illustrates several alternative embodiments of a sensor in an AED monitoring device.

FIG. 4 illustrates several alternative embodiments of a sensor operable to detect a non-audible parameter from an AED 100 annunciator activation. Sensor 304 may be one of several technologies as part of the monitoring device 300. It is understood that circuitry and processing by hardware processor 306 may differ somewhat between technologies, but also falls within the scope of the invention.

Sensor 304 may be a temperature sensor 402. It is known that beeper 122 heats slightly during activation, the temperature change being induced by the rapid vibratory motion of the annunciator diaphragm. Therefore, temperature sensor 402 is arranged closely adjacent to the beeper 122 diaphragm, and is selected with sufficient sensitivity to detect a pre-determine temperature change over a time interval that corresponds to the known "chirp" or series of chirps. Hardware processor 306 processes the corresponding signal, for example by comparing a known temperature response of the beeper 122 during a "chirp" or Beep Sequence 202 to the sensor signal. If the comparing step is a match, then a diaphragm motion of the beeper 122 is indicated. Hardware processor 306 then provides a corresponding signal to the output.

Alternatively, sensor 304 may be a vibration sensor 404. One embodiment of vibration sensor 404 is an accelerometer which is mounted on the printed circuit assembly, or one that is integrated with the hardware processor 306. Vibration sensor 404 is arranged to detect vibrations induced on the AED case 102 and enabled by the case 102 coupling with beeper 122. In this embodiment, hardware processor 306 compares a sensed frequency, duration and/or repetition pattern of vibrations to known parameters to determine whether the annunciator has activated.

Vibrational coupling of vibration sensor 404 with AED case 102 may optionally be improved by arranging a shorting coupler 410 between vibration sensor 304 and case 102. Shorting coupler 410 is preferably arranged to rest against case 102 when installed with monitoring device 300. Shorting coupler 410 may be hard "whiskers", prongs or other devices known to provide good vibrational coupling between objects.

Alternatively, sensor 304 may be an optical sensor 406. Optical sensor 406 preferably includes a light which illuminates either the annunciator diaphragm or an optically reflective surface on case 102. A photosensitive detector in optical sensor 304 is arranged to capture the reflected light and generate a corresponding electrical output signal. Optical sensor 406 thus detects any change in reflectance caused by changes in the diaphragm position during the diaphragm motion. One example of an optical sensor 406 is an LED laser diode-based optical transceiver, which includes both a laser diode light and a photo-sensor that is attuned to the laser diode frequency for enhanced sensitivity and noise suppression.

An alternative arrangement includes an optically reflective decal 302 that may be applied around beeper 122 such that optical sensor 406 detects changes in the decal 302 position induced by the annunciator-induced vibrations coupled to case 102. Thus, the positioning of the optical sensor 406 relative to the annunciator diaphragm is not so sensitive.

Alternatively, sensor 304 may be a capacitive sensor 408 which senses motion of the annunciator diaphragm that indicates activation. Capacitive sensor 408 may be disposed in one of three ways. If sensitive enough, capacitive sensor 408 may be located directly over the annunciator port in AED case 102. Alternatively, capacitive sensor 408 may be disposed on the end of a flexible stem which extends into the case 102 port hole to place the capacitive sensor 408 closer to the diaphragm. Alternatively, an electrically conductive decal may be applied to the defibrillator surface adjacent the annunciator. Capacitive sensor 408 is then disposed adjacent the decal, and can thus detect an annunciator-induced vibration of the AED 100 surface.

Figure 5:
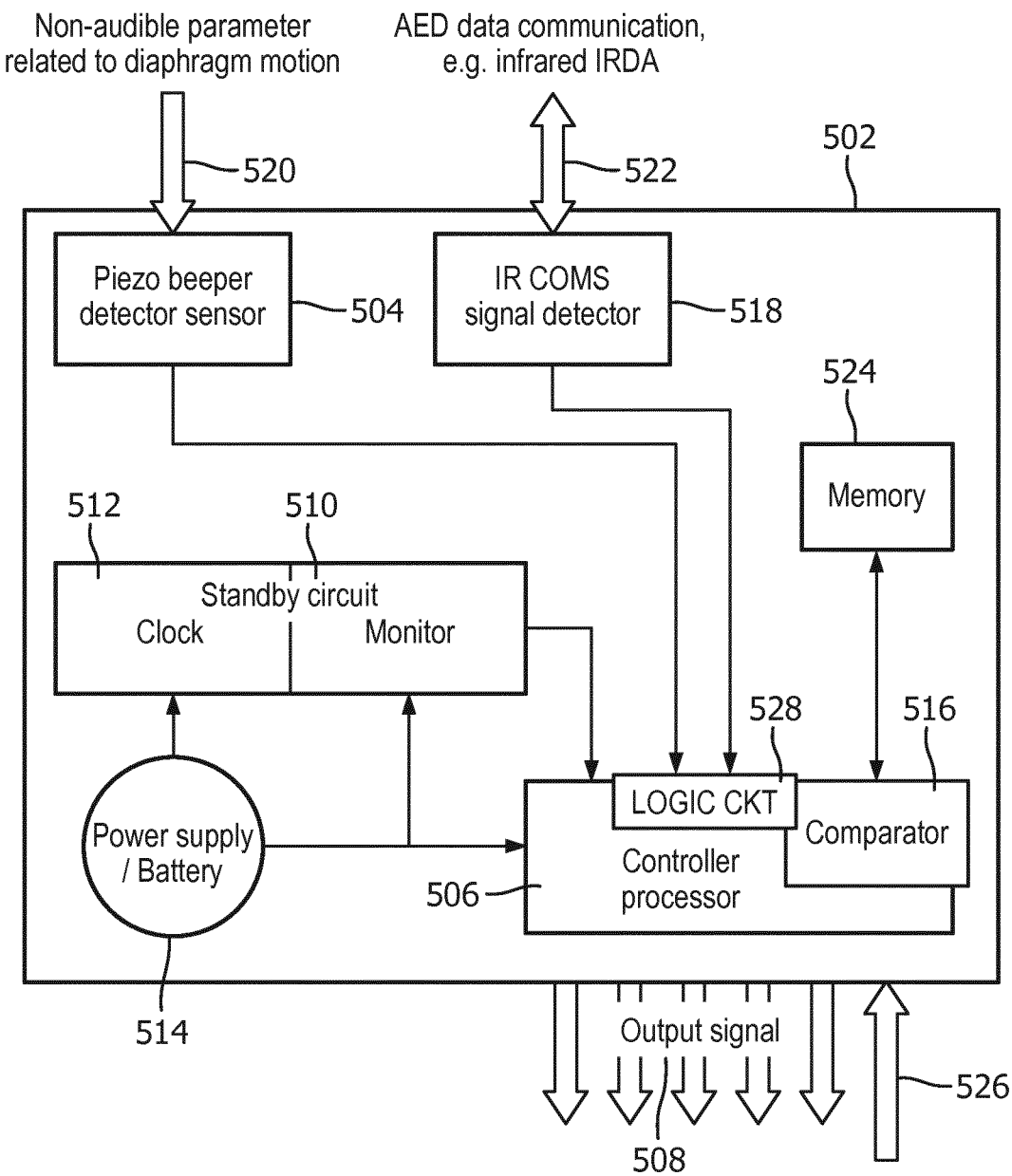
FIG. 5 illustrates an exemplary block diagram of the monitoring device for sensing an operating status of a defibrillator, the defibrillator having an audible annunciator with a diaphragm.

FIG. 5 illustrates an exemplary block diagram of the monitoring device for sensing an operating status of a defibrillator, the defibrillator having an audible annunciator with a diaphragm. Monitoring device 502 includes several elements. Although shown as functional blocks, each element is enabled by structure such as circuitry interconnected on a substrate by wire traces, semi-conductor processors and memory, and sensing devices. The elements may be controlled by software instructions residing in memory and being executed in one or more of the processors.

Monitoring device 502 obtains an input indicating the activation of the associated AED 100 annunciator at diaphragm motion parameter 520, which is a non-audible related parameter. Sensor 504, of a type previously described, captures the input. Sensor 504 passes the signal via electrical communication to the hardware processor 506. Hardware processor 506 analyzes the signal, and if the analysis indicates a signal corresponding to diaphragm motion, the processor provides an output 508.

Signal analysis may be conducted with a comparator 516 and a computer storage memory 524, consisting of a non-transitory medium or the like. Memory 524 stores data corresponding to a known characteristic of the annunciator, such as the aforementioned frequency, duration, repetition rate data, and known temperature and heating profiles. Comparator 516 compares the characteristics profile to the received parameter. Correlation within a detection threshold indicates a signal corresponding to diaphragm motion. Optionally, hardware processor 506 may store data indicative of the detected diaphragm motion, such as number of chirps, type of alert detected, and a cumulative number of chirps or operations of the diaphragm detected, for later use in diagnostics and trouble-shooting.

Also included in monitoring device 502 is a low-power standby circuit 510 which may include a clock 512 and a state change monitor. The standby circuit 510 maintains the monitoring device 502 in a very low-power standby mode of operation in order to maximize the life of the monitoring device 502 battery 514. Preferably, clock 512 activates the standby circuit 510 for a predetermined time duration on a predetermined schedule that corresponds to a self-testing periodicity of the AED 100. Thus, the monitoring device 502 is active only for those periods when AED 100 is also active and performing its self-test. After monitoring device 502 ascertains the status of the AED 100, and passes any necessary notifications to output 508, standby circuit 510 returns the hardware processor 506 to the low-power standby mode of operation.

Also included in monitoring device 502 is an optional second sensor 518 which is in communication with hardware processor 506. Second sensor 518 is disposed adjacent AED 100 such that it is operable to sense an AED data signal 522 output from the defibrillator. The data communication may be from wireless RF, so second sensor 518 may be a Wi-Fi, Near Field Communication (NFC), Bluetooth™ receiver or the like. The data communication might also be optical, such as from infrared data communication (IRDA), so second sensor 518 may be an IrDA receiver. Standby circuit 510 may optionally be triggered to activate hardware processor 506 based on a detected AED data signal 522. Because the AED data signal 522 is typically transmitted when the AED 100 activates, hardware processor 506 may adjust the predetermined periodicity and the timing of the next wake-up activation based on this sensed wireless data communication.

A communicator signal 526 may optionally be included as another input to monitoring device 502. This data pathway may enable to monitoring device 502 to further adjust itself or the AED 100 via AED data signal 522 based on a communication from a remote provider. For example, communicator signal 526 may signal hardware processor 506 to transmit all collected maintenance data held within memory 524.

Figure 6:
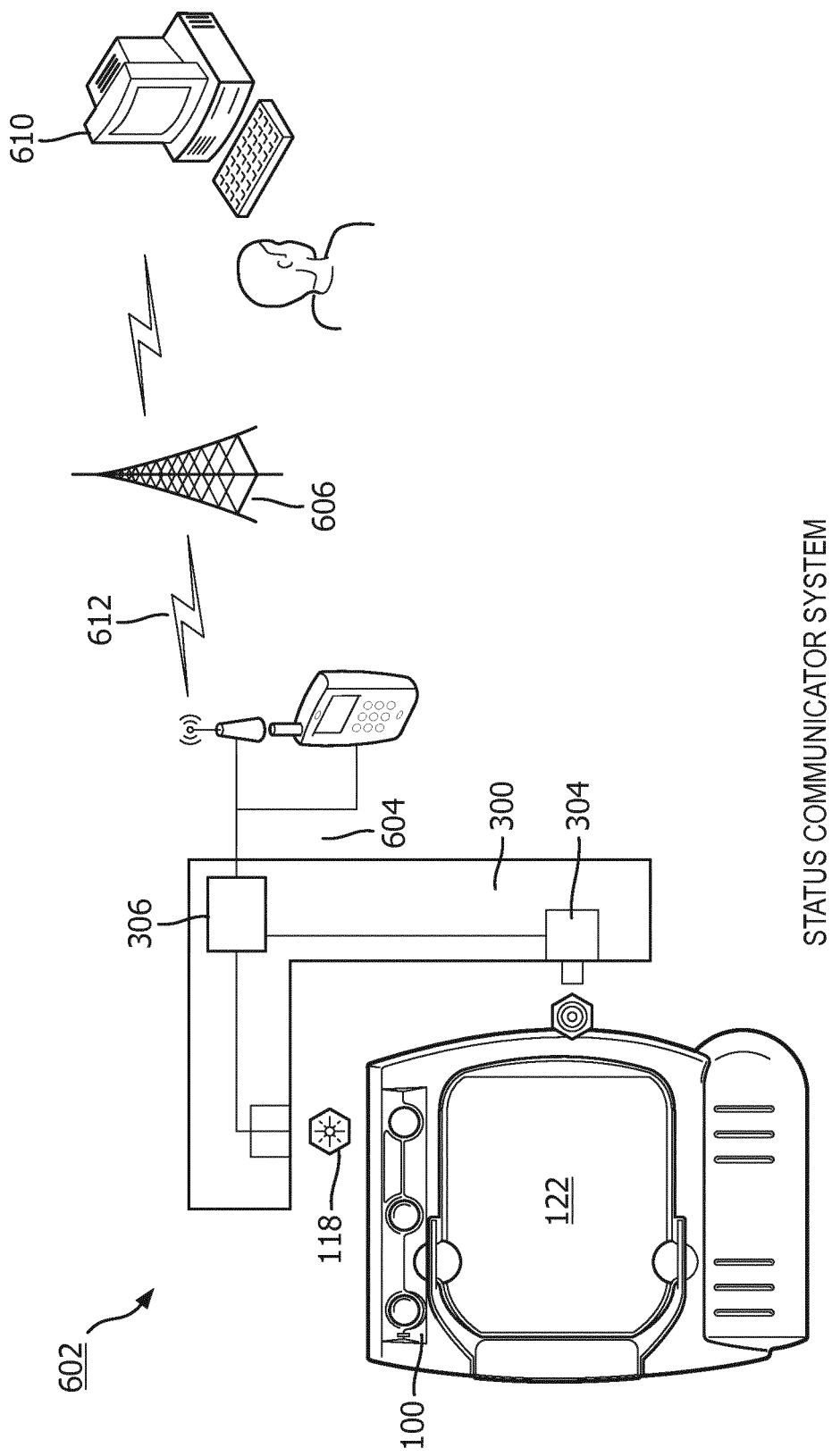
FIG. 6 illustrates a system for maintaining a defibrillator from a remote location, in accordance with one embodiment.

FIG. 6 illustrates a Status Communicator System 602 for maintaining a defibrillator from a remote location, in accordance with one embodiment of the invention. The system comprises four main components in addition to the monitored defibrillator or AED 100. The monitoring device 300, as previously described, includes a sensor 304 that is operable to detect a non-audible parameter related to the motion of a beeper 122 diaphragm. Sensor 304 sends a signal to hardware processor 306 which in turn provides a status signal via output 308 to a wireless transmitter 604.

Wireless transmitter 604 is the second component of the Status Communicator System 602. Preferably, wireless transmitter 604 is a standard communication device such as a smartphone or a Wi-Fi network node, the device adapted to include means for receiving an input from monitoring device 300. The input means may be a USB cable, a custom hardwire ribbon cable, a NFC/Bluetooth™ wireless connection, or a similar interface. Wireless transmitter 604 preferably maintains its own power supply, and has software which executes instructions to transmit defibrillator status information on a periodic or as-needed basis. Accordingly, 604 transmits a defibrillator status report transmission 612 over a wireless network 606 to a remote receiver 610. There, a service provider can take any needed corrective action, such as contacting the AED 100 owner or initiating a service call. Optionally, the Status Communicator System 602 may be bi-directional so that the 610 may transmit a reply message back to 604 for display on a screen associated with the wireless transmitter 604, monitoring device 300, or AED 100. The return message may also be a control signal which changes the status of AED 100 or monitoring device 300 to accommodate the nature of the detected failure.

Figure 7:
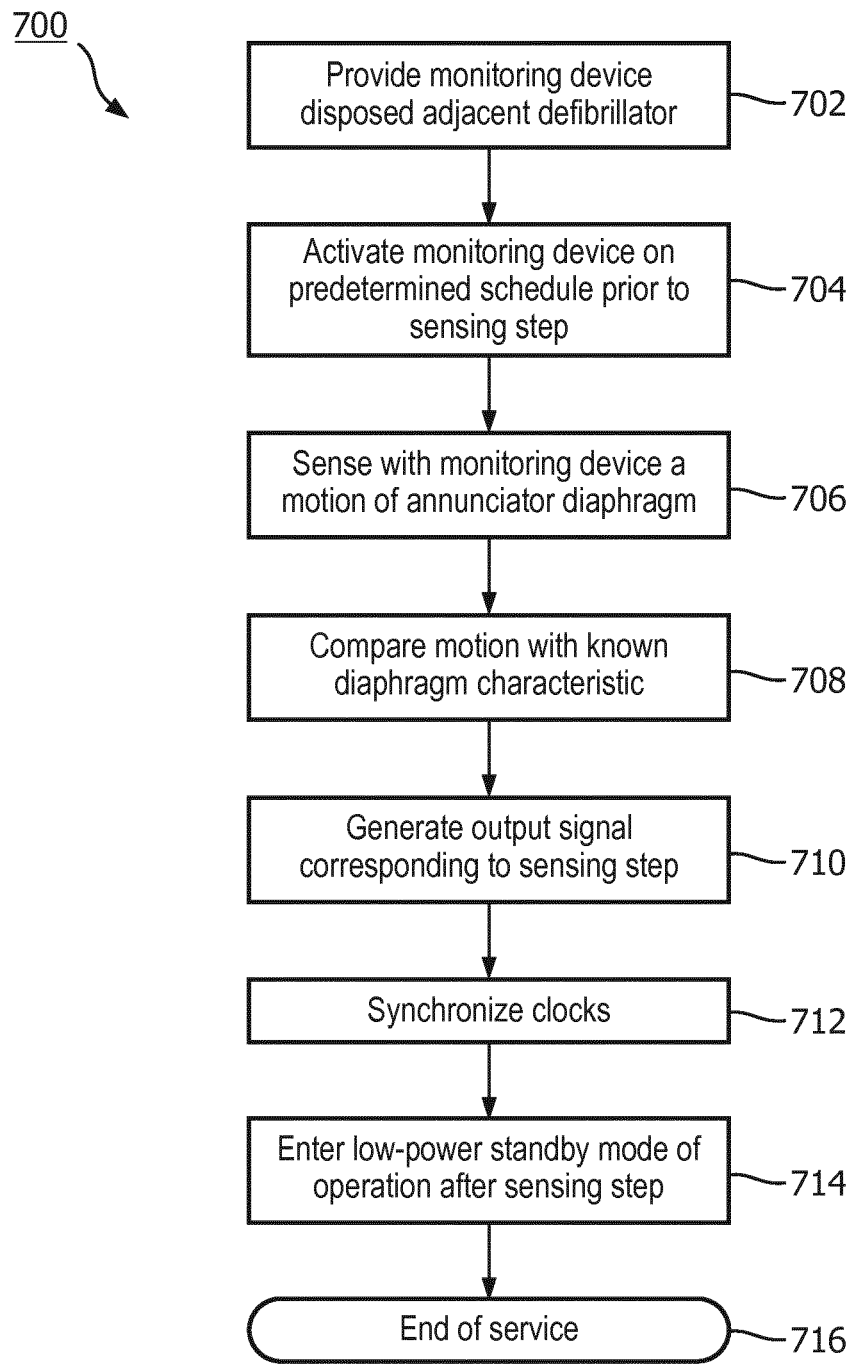
FIG. 7 illustrates a method for monitoring an AED 100 in accordance with one embodiment.

FIG. 7 illustrates a method of sensing an operating status of a defibrillator having an audible annunciator with a diaphragm 700. The method 700 begins with a providing step 702 of providing a monitoring device according to the present inventive apparatus, wherein the monitoring device is preferably disposed adjacent the defibrillator, including as an integral part of the defibrillator storage case or wall mount. The monitoring device 300 is placed into service, preferably in a low-power standby mode, and begins to operate according to a predetermined schedule. Monitoring device 300 may be synchronized with AED 100 at this step, either manually or automatically, for example by activating immediately and remaining activated until the monitoring device 300 senses the next AED 100 activation, after which both devices re-enter a low-power standby mode of operation.

At step 704, the monitoring device 300 activates itself. The preferred method of activation is according to a predetermined schedule or periodicity. The schedule and periodicity is even more preferably corresponding to a known self-testing periodicity of AED 100. Alternatively, the monitoring device 300 may activate on a multiple of the AED 100 self-testing periodicity, such as every two or three periodic self-tests, in order to further conserve monitoring device 300 battery power. In order to maintain synchronization between monitoring device 300 and AED 100, the monitoring device 300 clock may be adjusted at an activation to match the AED 100 timer.

In sensing step 706, the activated monitoring device senses a motion of the adjacent AED 100 annunciator, according to one of the embodiments of the previous apparatus description. For example, the sensing step 706 may be an optical or capacitive sensing of the diaphragm motion, a temperature excursion in the annunciator induced by activation, or a sensing of mechanical vibration of the AED 100 case induced by the annunciator. A lack of sensing within a predetermined time during the cause the method to either proceed to a corresponding output step 710, or re-enter the low-power standby mode at step 714 until the next scheduled activation.

At optional comparing step 708, a characteristic of the sensed motion from sensing step 706 is compared to a known characteristic of the activated annunciator diaphragm, by one of the methods as previously described. If the hardware processor 306 in comparing step 708 determines a match, then an activation is indicated to the generating step 710.

Generating step 710 generates an output signal corresponding to sensing step 706 and/or comparing step 708. An output signal is preferably provided by the monitoring device 300 to an associated wireless transmitter 604 which in turn sends a corresponding wireless communications signal to a remote receiver. Alternatively, the output signal is provided to computer storage memory 524 to maintain a record of the operating performance, or to allow signals to be deferred to save system power or to reduce nuisance alarms.

Optional synchronizing step 712 is conducted by the monitoring device 300 before it returns to a low-power standby mode of operation. In this step, monitoring device 300 adjusts its next "wake-up" activation to the next AED 100 self-test activation time, based upon the start of the sensed second sensor 318 output, such as a periodic informational IRDA message output.

After performing the above method steps, monitoring device 300 returns to a low-power standby mode of operation at entering low-power standby mode step 714, and awaits the next scheduled activating step 704. The method may end at step 716 if the AED and/or monitoring device 300 is taken out of service.

Figure 8:
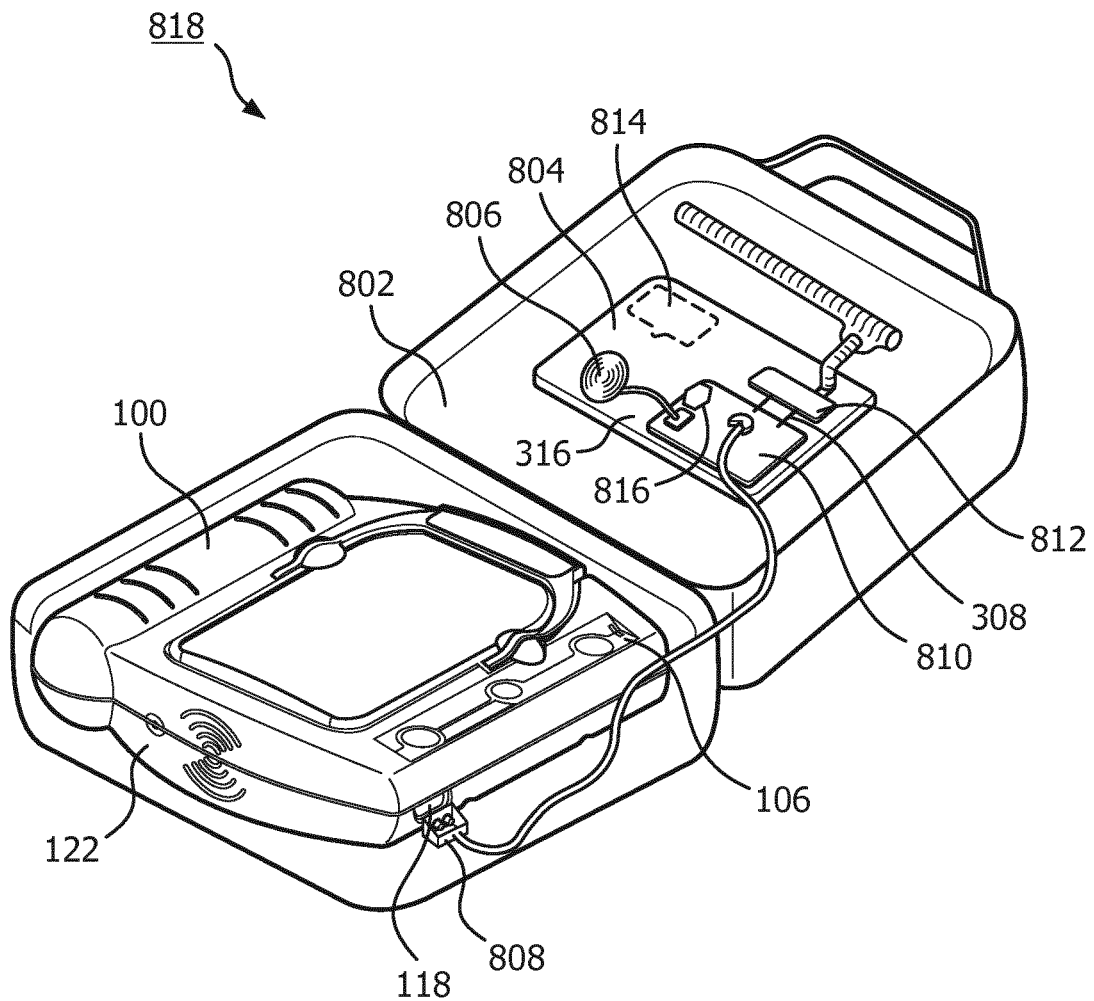
FIG. 8 illustrates an aspect of the subject matter apparatus in accordance with one embodiment.

FIG. 8 illustrates the local portion of a system 818 for monitoring and communicating the readiness status of an AED. System 818 generally includes an AED 100 and a monitoring device 804 that is disposed externally to and adjacent the AED. Monitoring device 804 includes two or more sensors which detect outputs from the AED 100 that can be used to determine the readiness of the AED for use. As can be seen in FIG. 8, all AED, monitoring, and sensing components are contained within a carrying case 802. Carrying case 802 may be arranged such that monitoring device 804 may be retained in a lid portion of the case, and out of the way of the AED 100 and other accessories that are needed for use. FIG. 8 indicates that the monitoring device 804 could be sized to fit within a space otherwise filled by a spare battery. Thus, substrate 316 may be sized appropriate to the desired space. Presumably, the monitoring and notification functions of the monitoring device 804 would eliminate and replace the need for having a spare battery with the device.

Monitoring device 804 may be similar to monitoring device 300 and monitoring device 502 in several aspects. Monitoring device 804 may be powered with a battery power supply 814 which is independent of the AED 100 power supply. Preferably, power supply 814 has a normal operational life approximately equivalent to the AED power supply, and is thus sized to power monitoring device 804 functions for between three and five years.

Monitoring device 804 may also include a hardware processor 810 and standby circuit and clock 816 that is similar to the components previously described. Standby circuit and clock 816 is operable to activate the hardware processor 810 for a predetermined time and on a predetermined periodicity to maximize battery life. In one embodiment, the predetermined periodicity corresponds to a known self-testing periodicity of AED 100. Hardware processor 810 may additionally be operable to synchronize the predetermined periodicity with the self-testing periodicity based on a sensed AED wake-up time. Standby circuit and clock 816 preferably maintains the hardware processor 810 in a low-power standby mode of operation outside of the predetermined periods in order to maximize battery life.

Likewise, wireless transmitter 812 with antenna may be similar to wireless transmitter 604. AED status output 308 may also be communicated from hardware processor 810 to wireless transmitter 812 in a manner described previously. Hardware processor 810 may include a computer storage memory 524 that stores data indicative of AED 100 status for later output and/or wireless transmission.

FIG. 8 also illustrates that monitoring device 804 need not be physically disposed next to both of AED beeper 122 and infrared port 118. In this embodiment, the activation of beeper 122, also referred to here as a fault indicator, may be detected by a fault indicator sensor 806 disposed on substrate 316 and comprised of a microphone that detects the beeper 122 chirps. Thus fault indicator sensor 806 need only be disposed within audible range of beeper 122. Of course, fault indicator sensor 806 can be comprised like sensor 304 if so desired. Fault indicator sensor 806 provides the activation indication to hardware processor 810.

Power sensor 808 can also be disposed away from monitoring device 804. In this embodiment, power sensor 808 comprises a sensor arranged to detect an IRDA output from the defibrillator, and is communicatively attached to hardware processor 810 via a cable. Alternatively, power sensor 808 comprises an optical sensor arranged to detect the flashing of ready light 106 if AED 100 does so for normal readiness conditions. Other embodiments of fault indicator sensor 806 include an optical sensor arranged to detect an LCD readiness icon, a photoelectric sensor arranged to detect a flashing indicator light, a camera arranged to detect a defibrillator display panel, and a magnetic sensor arranged to detect an electromechanical status indicator signal.

Referring back to FIG. 6, the local portion of the defibrillator status communicator system interacts with the remote portion by transmitting from the wireless transmitter 812 a defibrillator status report transmission 612 that corresponds to the previously described status signal. The remote portion in turn is a remote service provider computer having a remote receiver 610 that is operable to receive the defibrillator status report. In a preferred embodiment, the remote service provider computer, upon receipt of a status report indicative of an AED fault, automatically generates a service alert message to initiate corrective action.

Figure 9:
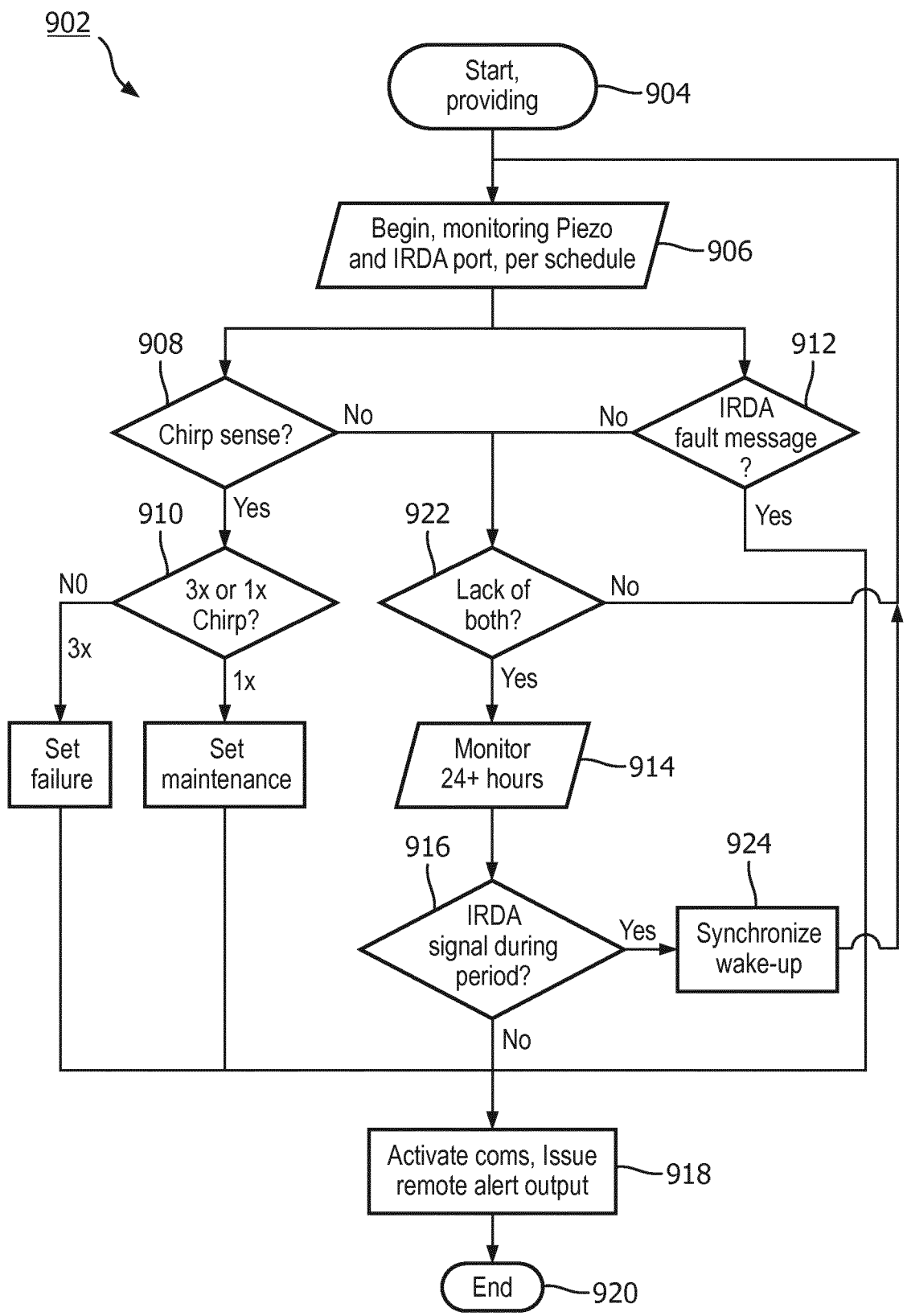
FIG. 9 illustrates a method for sensing a defibrillator operating status 902 according to another embodiment of the subject matter.

Monitoring device 804 operates according to the following method 902 for sensing an operating status of a defibrillator having both of a fault indicator 122 and a power supply indicator 118. The method is illustrated in FIG. 9.

The method 902 begins with the step 904 of providing a monitoring device disposed adjacent the defibrillator, in accordance with the embodiments of the apparatus that are described previously. The monitoring device may include a fault indicator sensor disposed adjacent the defibrillator fault indicator and operable to detect an activation of the fault indicator, a power sensor disposed adjacent the defibrillator power supply indicator and operable to detect an activation of the power supply indicator, a hardware processor in electrical communication with both of the fault indicator sensor and the power sensor, and an output in communication with the hardware processor for providing a signal indicative of the defibrillator operating status. In some embodiments, such a method may further include providing a transmitter in communication with the monitoring device hardware processor. An optional memory 524 may also be provided as previously described, for retaining defibrillator status information for archiving or later transmission.

Providing step 904 is completed by assembling the system together and initiating its operation. One portion of initiating its operation may be in synchronizing the "wake-up" operations of the monitoring device 300 and the defibrillator. This may be done manually by setting the monitoring device clock, or automatically by activating the monitoring device until it detects the next defibrillator wake-up. At that time and following an initial check, the monitoring device may enter a low-power standby mode of operation until approximately the next pre-determined and scheduled defibrillator wake-up.

Monitoring according to the predetermined schedule begins at step 906. Monitoring device 804 activates itself preferably just prior to a scheduled activation of the adjacent defibrillator. Monitoring device 804 then begins sensing over an interval of a predetermined period of time, wherein the fault indicator sensor 806 and the power sensor 808 sense outputs from the defibrillator fault indicator and power supply indicator respectively. One exemplary predetermined period of time is for approximately eight seconds on a daily basis, i.e. every twenty-four hours. The time period in any case should be selected such that it is assured that the monitoring device 804 will detect any periodic activation of the fault indicator and the power supply indicator. Of course the particular time period will depend on the pre-determined schedule in the underlying defibrillator, such as corresponding to a scheduled self-test activation time of the defibrillator.

In an alternate embodiment, a predetermined period for the fault indicator sensor may not fully correspond to a second predetermined period of time for the power sensor. This alternate schedule may be desired for reasons of battery power conservation in the monitoring device, or for more rapid fault detection. For example, the monitoring device 804 may awaken more often, but for briefer duration to sense for a fault indicator "chirp". But monitoring device 804 may also awake at other times, but for a longer duration to detect a message stream issuing from the power supply sensor.

While activated, monitoring device 804 may monitor for three different conditions: a chirp fault sensing, a power supply fault sensing, and a lack of any sensed output from the defibrillator for a period of time that may indicate a completely dead defibrillator.

At chirp sense step 908, the fault indicator sensor senses an activation, or a lack of an activation, of the fault indicator for the predetermined period of time. A sensed activation may be a single chirp or multiple chirps of the fault indicator, which is additionally detected at chirp type step 910. A triple chirp 3× may indicate that the defibrillator has failed and is inoperative for a rescue. A single chirp 1× may indicate that the defibrillator can be used for a rescue but that it requires corrective attention. The information about fault indicator activation, type, or lack thereof, is provided to hardware processor 810.

At power supply indicator sense step 912, the power sensor senses an activation, or a lack of an activation, of the power supply indicator for either the predetermined period of time or a second predetermined period of time, depending on the device scheduling. The power sensor may comprise an optical sensor arranged to detect a flashing light defibrillator power supply indicator. The power sensor may also be configured to capture a power supply indicator fault indication, such as an IRDA message encoded in the power sensor output. Information about the power supply indicator activation, message type, or lack thereof, is provided to hardware processor 810.

It may be possible that the monitored defibrillator is completely non-functional while consequently providing no fault indication at all, or that an error of synchronization between monitor device and defibrillator has occurred that prevents any fault detection. In these cases, it may further be possible that monitoring device 804 may erroneously interpret the lack of any fault indication as indicating a "good" defibrillator. A dead battery sensing step 922 assures that such an error does not occur. If no activation is sensed at both chirp sense step 908 and power supply indicator sense step 912 during the predetermined period(s) of time, then a dead battery condition is indicated.

Optionally, the hardware processor 810 may hold the monitoring device 804 activated at confirming step 914 to confirm the dead battery condition. Thus, monitoring device 804 will continuously monitor for a defibrillator signal for a third predetermined period of time, such as for twenty four hours, or until a signal from the defibrillator is received.

Information about any sensed activation, or lack thereof, for this third extended period of time is provided to hardware processor 810. If a power supply 814 signal or a fault indicator signal is not sensed by monitoring device 804 at synchronization error step 916, then a dead battery condition exists. The monitoring device 804 generates a corresponding status output signal.

On the other hand, if monitoring device 804 senses a power supply indication at synchronization error step 916, an synchronization error between defibrillator and monitoring device is indicated. A sensed indication at synchronization error step 916 initiates a routine at synchronization step 924 to bring the defibrillator self-testing schedule into correspondence with the monitoring device 804 activation schedule. Then the method returns to the monitoring step 906 in preparation for the next scheduled activation.

Method for sensing a defibrillator operating status 902 continues at generating status output signal step 918, having received one or more indications of a defibrillator fault or failure. As described above, a defibrillator failure operating status output signal is generated at step 918 in response to a chirp sensing, a power sensor sensing, or a confirmed lack of sensing from both sensors. The nature of the output signal may be a local indication at monitoring device 804, such as a light or an aural alarm. Preferably, step 918 further comprises a transmitting step for transmitting a failure status message to a remote service provider. Such a transmission may be one already known in the art, such as a wired telephonic or internet transmission, a wireless telephony transmission, or a wireless short-range transmission (e.g.

B-field, Bluetooth™, near field communication NFC) to an intermediate transmitting device such as a smartphone.

Ending step 920 may comprise placing the operating status message into the device memory 524 for archiving and later retrieval. Generally, the method then returns to monitoring step 906 to repeat the process per the schedule.

The invention claimed is:

1. A monitoring device for sensing an operating status of a defibrillator having both of a fault indicator and a power supply indicator, comprising:
   a substrate arranged to be disposed adjacent the defibrillator;
   a fault indicator sensor disposed adjacent the defibrillator fault indicator and suitably configured to detect an activation of the fault indicator;
   a power sensor disposed on the substrate and adjacent the defibrillator power supply indicator and suitably configured to detect an activation of the power supply indicator;
   a hardware processor disposed on the substrate and in electrical communication with both of the fault indicator sensor and the power sensor;
   an output in communication with the hardware processor for providing a signal indicative of the defibrillator operating status, wherein the hardware processor executes software instructions which controls the signal based on both of a sensed lack of an activation of the fault indicator by the fault indicator sensor for a predetermined period of time and a second sensed lack of the power supply indicator by the power sensor for a second predetermined period of time that corresponds to a scheduled self-test activation time of the defibrillator; and
   a transmitter in controllable communication with the hardware processor, wherein the transmitter is controllably operable to transmit a defibrillator failure operating status message responsive to the signal indicative of the defibrillator operating status.

2. The monitoring device of claim 1, wherein the fault indicator sensor comprises one selected from the group of a microphone and a sensor operable to detect a non-audible parameter related to a diaphragm motion of a fault indicator diaphragm.

3. The monitoring device of claim 1, wherein the power sensor further comprises an optical sensor arranged to detect a lighted defibrillator power supply indicator.

4. A monitoring device for sensing an operating status of a defibrillator having both of a fault indicator and a power supply indicator, comprising:
   a substrate arranged to be disposed adjacent the defibrillator;
   a fault indicator sensor disposed adjacent the defibrillator fault indicator and suitably configured to detect an activation of the fault indicator;
   a power sensor disposed on the substrate and adjacent the defibrillator power supply indicator and suitably configured to detect an activation of the power supply indicator;
   a hardware processor disposed on the substrate and in electrical communication with both of the fault indicator sensor and the power sensor;
   a low-power standby circuit with a clock, the low power standby circuit in communication with the hardware processor and operable to activate the hardware processor for the predetermined time on a predetermined periodicity; and
   an output in communication with the hardware processor for providing a signal indicative of the defibrillator operating status, wherein the hardware processor executes software instructions which controls the signal based on both of a sensed lack of an activation of the fault indicator by the fault indicator sensor for a predetermined period of time and a second sensed lack of the power supply indicator by the power sensor for a second predetermined period of time that corresponds to a scheduled self-test activation time of the defibrillator.

5. The monitoring device of claim 4, wherein the predetermined periodicity is about eight seconds on a daily basis.

6. The monitoring device of claim 5, wherein the power sensor is operable to sense one of a wireless data communication and an infrared data communication (IRDA) output from the defibrillator, wherein the hardware processor is operable to adjust the predetermined periodicity based on the sensed output from the defibrillator.

7. The monitoring device of claim 5, wherein the hardware processor enters a low-power standby mode of operation after the predetermined time.

8. The monitoring device of claim 1, further comprising a computer storage memory in communication with the hardware processor and the output, wherein the computer storage memory stores data indicative of the fault indicator sensor detection and the power sensor detection.

9. A defibrillator status communicator system comprising:
   a defibrillator having a fault indicator output and a power supply indicator output;
   an electronic monitoring device disposed external to the defibrillator and adjacent to both of the fault indicator output and the power supply indicator output, further comprising a fault indicator sensor operable to detect an activation of the fault indicator output, a power sensor operable to detect an activation of the power supply indicator output, a hardware processor in electrical communication with both of the fault indicator sensor and the power sensor, and an output in communication with the hardware processor for providing a signal indicative of a lack of detection of both of an activation of the fault indicator output and the power supply indicator output for a predetermined period of time that corresponds to a scheduled self-test activation time of the defibrillator; and
   a wireless transmitter in communication with the output, the transmitter operable to transmit a defibrillator status report based on a function of the signal.

10. The system of claim 9, further comprising a remote service provider computer in wireless communication with the wireless transmitter and operable to receive the defibrillator status report, wherein the remote service provider computer automatically generates a service alert message responsive to the defibrillator status report.

11. The monitoring device of claim 4, wherein the fault indicator sensor comprises one selected from the group of a microphone and a sensor operable to detect a non-audible parameter related to a diaphragm motion of a fault indicator diaphragm.

12. The monitoring device of claim 4, wherein the power sensor further comprises an optical sensor arranged to detect a lighted defibrillator power supply indicator.

13. The monitoring device of claim 4, further comprising a computer storage memory in communication with the hardware processor and the output, wherein the computer storage memory stores data indicative of the fault indicator sensor detection and the power sensor detection.

\* \* \* \* \*